(12) United States Patent
Finnestad

(10) Patent No.: US 8,505,769 B2
(45) Date of Patent: Aug. 13, 2013

(54) MEDICAL WASTE RECEPTACLE

(75) Inventor: Mark Brian Finnestad, Franklin, MA (US)

(73) Assignee: Covidien LP, Mansfield, MA (US)

( * ) Notice: Subject to any disclaimer, the term of this patent is extended or adjusted under 35 U.S.C. 154(b) by 355 days.

(21) Appl. No.: 12/853,391

(22) Filed: Aug. 10, 2010

(65) Prior Publication Data

US 2012/0037626 A1 Feb. 16, 2012

(51) Int. Cl.
B65D 81/00 (2006.01)

(52) U.S. Cl.
USPC .......................................... 220/908; 206/366

(58) Field of Classification Search
USPC .............. 220/908, 521, 254.9; 232/30, 31, 232/32, 45, 62, 57, 47, 60, 58; 206/366, 206/370, 362
See application file for complete search history.

(56) References Cited

U.S. PATENT DOCUMENTS

| 4,453,648 A | 6/1984 | Harris et al. |
| 4,580,688 A | 4/1986 | Harris et al. |
| 4,714,168 A | 12/1987 | Johnson et al. |
| 4,715,498 A | 12/1987 | Hanifl |
| 4,779,728 A | 10/1988 | Hanifl et al. |
| 4,890,733 A | 1/1990 | Anderson |
| 5,076,429 A * | 12/1991 | Patrick et al. .................. 206/370 |
| 5,154,345 A | 10/1992 | Shillington |
| 5,240,108 A * | 8/1993 | Tonna ............................ 206/366 |
| 5,346,086 A | 9/1994 | Harris |
| 5,419,435 A | 5/1995 | Perzan et al. |
| 5,494,158 A | 2/1996 | Erickson |
| 5,494,186 A | 2/1996 | Marsh |
| 5,570,783 A | 11/1996 | Thorne et al. |
| 5,647,502 A | 7/1997 | Marsh |
| 5,848,692 A | 12/1998 | Thorne et al. |
| 5,947,285 A | 9/1999 | Gaba et al. |
| 6,250,465 B1 | 6/2001 | Daniels et al. |
| 6,283,909 B1 | 9/2001 | Sharp |
| 7,516,844 B2 | 4/2009 | Erickson et al. |
| 7,556,149 B2 | 7/2009 | Erickson et al. |
| 7,600,638 B2 | 10/2009 | Finnestad et al. |
| 7,694,822 B2 | 4/2010 | Sullivan et al. |
| 2012/0037628 A1 | 2/2012 | Finnestad |

* cited by examiner

*Primary Examiner* — Jeffrey Allen
(74) *Attorney, Agent, or Firm* — Lisa E. Winsor, Esq.

(57) ABSTRACT

A lid covering an interior of a medical waste receptacle base including a cover for covering the interior of the base. The cover has an opening for passing medical waste through it. The lid includes a chute for directing medical waste into the interior of the base and a closure for blocking the opening operatively connected to the cover for movement between an open position and a closed position. The lid includes a skirt operatively connected to the closure. The skirt sweeps medical waste on the chute toward the waste receptacle base interior as the closure moves from the closed position to the open position.

15 Claims, 4 Drawing Sheets

MEDICAL WASTE RECEPTACLE

FIELD OF THE INVENTION

The present invention relates to a medical waste receptacle, and more particularly to a receptacle having a skirt for clearing waste from a chute.

BACKGROUND

Healthcare providers and biomedical research facilities generate significant quantities of contaminated waste that is a potential source of disease and infection. Examples of such waste include syringes, needles, intravenous bags, catheters, wound care products, and other disposable patient care products. It is important that medical waste disposal containers limit access to their contents during use to prevent users from contacting the contaminated waste. Accordingly, there is a need for such containers.

SUMMARY

The present invention relates to a lid covering an interior of a medical waste receptacle base. The lid includes a cover sized and shaped for covering the interior of the medical waste receptacle base. The cover has an opening sized for passing medical waste through it. The lid also includes a chute extending below the cover opening for directing medical waste into the interior of the medical waste receptacle base. The lid also includes a closure sized for blocking the opening operatively connected to the cover for movement between an open position, in which the closure is at least partially out of alignment with the opening to allow medical waste to pass through the opening toward the interior of the medical waste receptacle base, and a closed position, in which the closure is aligned with the opening to block the opening to prevent medical waste from passing through the opening. The lid also includes a skirt operatively connected to the closure. The skirt sweeps medical waste on the chute toward the waste receptacle base interior as the closure moves from the closed position to the open position.

In another aspect, the present invention relates to a medical waste receptacle including a base having an interior sized and shaped for receiving medical waste. The medical waste receptacle also includes a cover sized and shaped for covering the interior of the base. The cover has an opening sized for passing medical waste through it. The medical waste receptacle also includes a chute extending below the cover opening for directing medical waste into the interior of the base. The medical waste receptacle also includes a closure sized for blocking the opening operatively connected to the cover for movement between an open position, in which the closure is at least partially out of alignment with the opening to allow medical waste to pass through the opening toward the interior of the base, and a closed position, in which the closure is aligned with the opening to block the opening to prevent medical waste from passing through the opening. The medical waste receptacle also includes a skirt operatively connected to the closure. The skirt sweeps the medical waste on the chute toward the waste receptacle base interior as the closure moves from the closed position to the open position.

In yet another aspect, the present intention includes a lid covering an interior of a medical waste receptacle base. The lid includes a cover sized and shaped for covering the interior of the medical waste receptacle base. The cover has an opening sized for passing medical waste through it. The lid also includes a chute extending below the cover opening for directing medical waste into the interior of the medical waste receptacle base. The lid also includes a closure sized for blocking the opening operatively connected to the cover for movement between an open position, in which the closure is at least partially out of alignment with the opening to allow medical waste to pass through the opening toward the interior of the medical waste receptacle base, and a closed position, in which the closure is aligned with the opening to block the opening to prevent medical waste from passing through the opening. The lid also includes a skirt operatively connected to the closure. The skirt is biased toward the chute for sweeping medical waste on the chute.

In a further aspect, the present invention includes a medical waste receptacle including a base having an interior sized and shaped for receiving medical waste. The medical waste receptacle also includes a cover sized and shaped for covering the interior of the base. The cover has an opening sized for passing medical waste through it. The medical waste receptacle also includes a chute extending below the cover opening for directing medical waste into the interior of the base. The medical waste receptacle also includes a closure sized for blocking the opening operatively connected to the cover for movement between an open position, in which the closure is at least partially out of alignment with the opening to allow medical waste to pass through the opening toward the interior of the base, and a closed position, in which the closure is aligned with the opening to block the opening to prevent medical waste from passing through the opening. The medical waste receptacle also includes a skirt operatively connected to the closure. The skirt is biased toward the chute for sweeping medical waste on the chute.

BRIEF DESCRIPTION OF THE DRAWINGS

Corresponding reference characters indicate corresponding parts throughout the drawings.

DETAILED DESCRIPTION OF THE DRAWINGS

Figure 1:
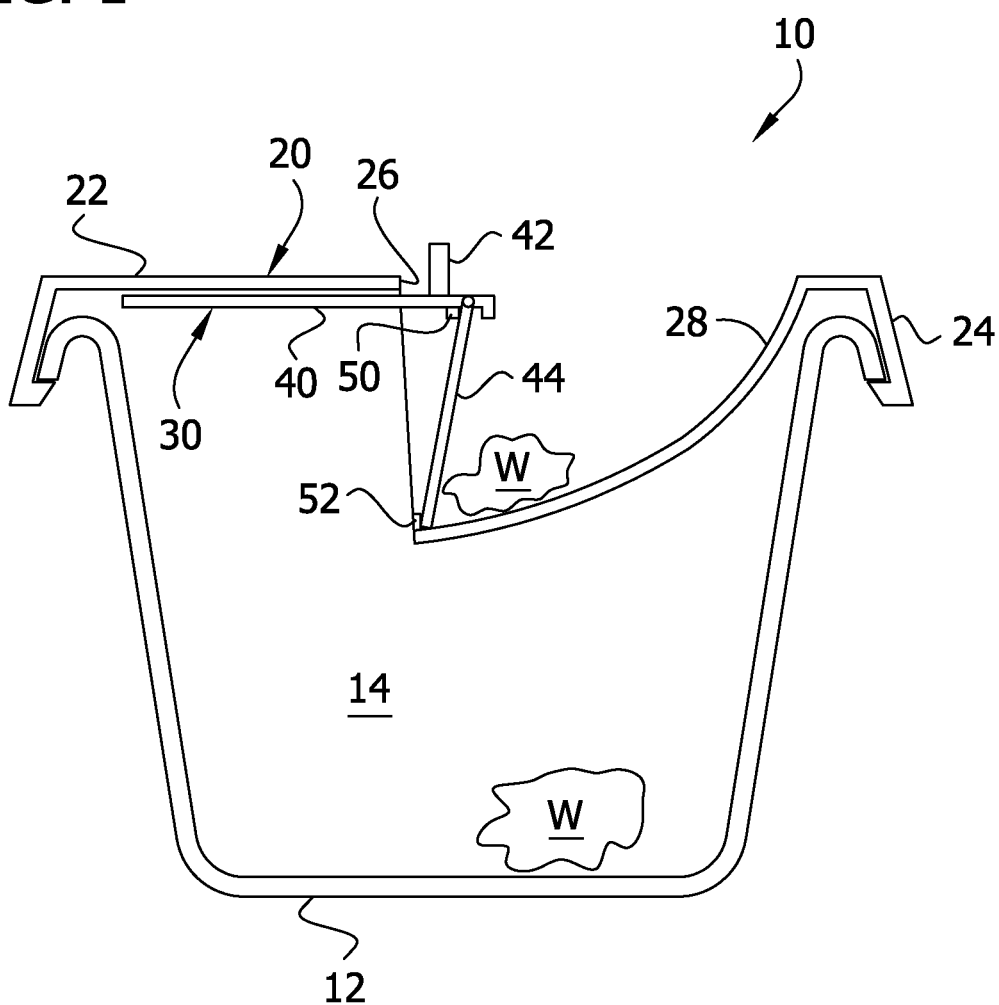
FIG. 1 is a vertical cross section of a medical waste receptacle of the present invention shown with a closure thereof in an open position.

Referring to FIG. 1, a medical waste receptacle is generally designated by the reference number 10. The receptacle 10 includes a base 12 having an interior 14 sized and shaped for receiving medical waste W. Medical waste W is stored in the interior 14 of the base 12 until the receptacle 10 is deemed ready for disposal using conventional procedures. The base 12 is conventional and will not be described in further detail. The receptacle also includes a lid, generally designated by 20, for covering the interior 14 of the base 12. The lid 20 may be removably or permanently attached to base 12. In one embodiment, lid 20 may be integrally formed with base 12.

The lid 20 includes a cover 22 sized and shaped for covering the interior of the medical waste receptacle base 12. The lid 20 has a rim 24 extending around the cover 22 for attaching the lid 20 to the base 12. The cover 22 has an opening 26 sized for passing medical waste W so a user can insert the waste into the interior 14 of the base without removing the lid 20 from the base 12. A chute 28 extends downward from the cover 22 immediately below the opening 26 to direct the medical waste W dropped through the opening downward into the interior 14 of the receptacle base 12.

Figure 3:
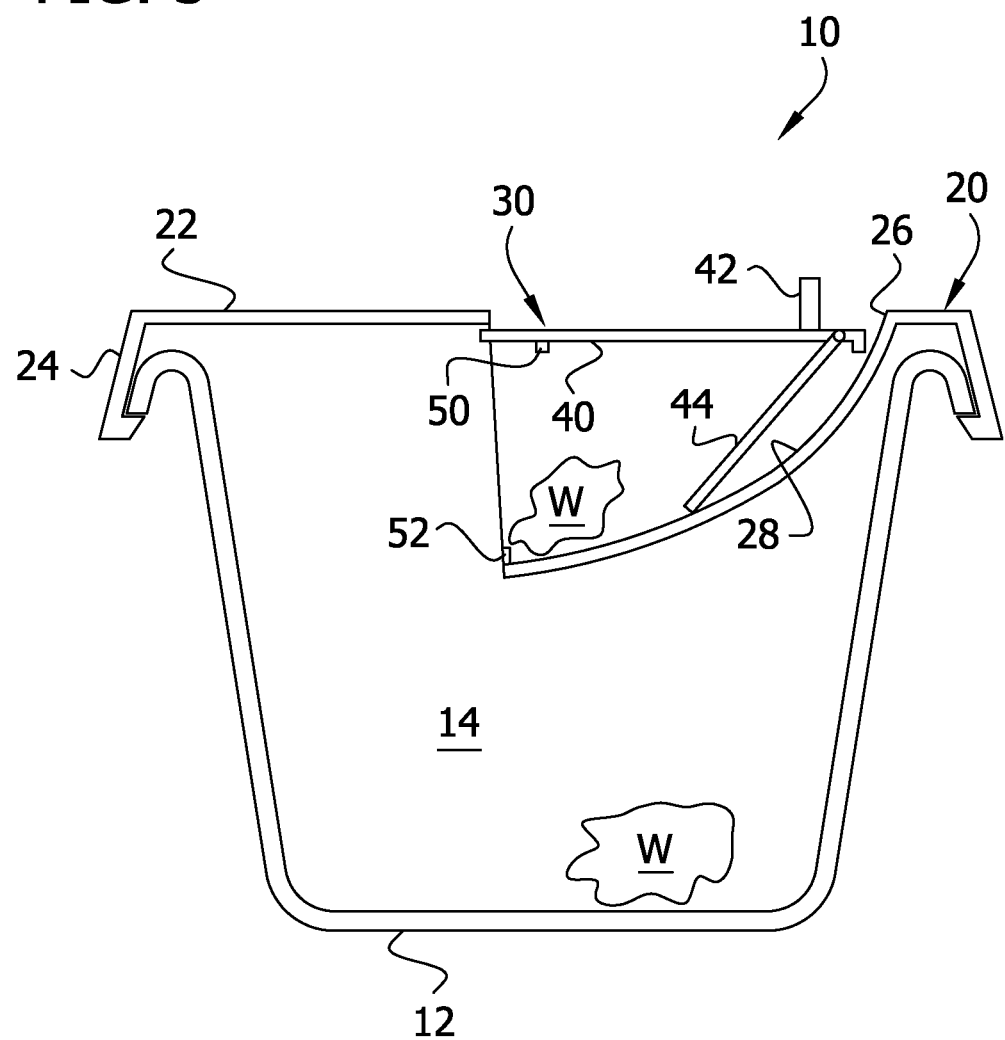
FIG. 3 is a vertical cross section of the receptacle with the cover in a closed position.
Figure 4:
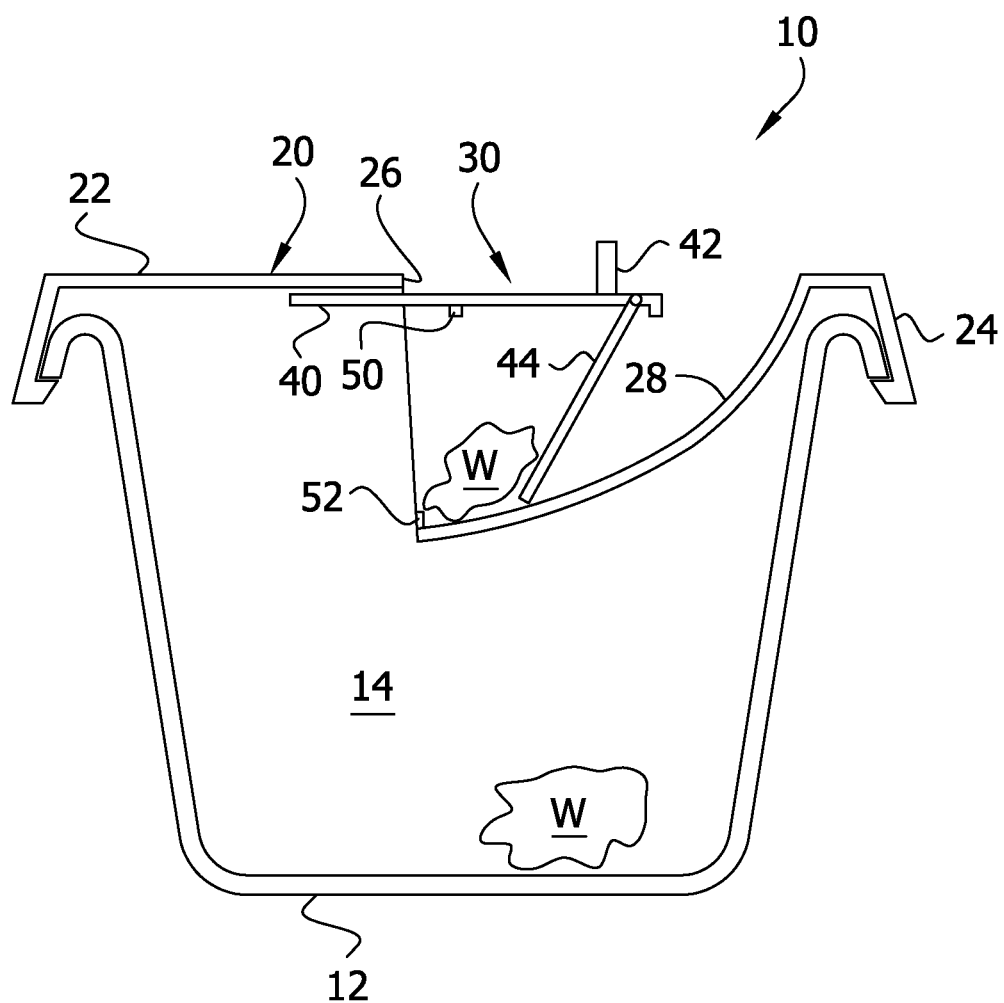
FIG. 4 is a vertical cross section of the lid with the cover in a partially opened position.

The lid 20 also includes a closure, generally designated by 30, sized for selectively blocking the opening 26 in the cover 22. The closure 30 is operatively connected to the cover 22 for movement between an open position as shown in FIG. 1 and a closed position as shown in FIG. 3. In the open position (FIG. 1), the closure 30 is at least partially out of alignment with the opening 26 in the cover to allow medical waste W to pass through the opening to the interior 14 of the base 12. In the closed position (FIG. 3), the closure 30 is aligned with the opening 26 in the cover 22 to block the opening and to prevent medical waste W from passing through the opening.

Figure 2:
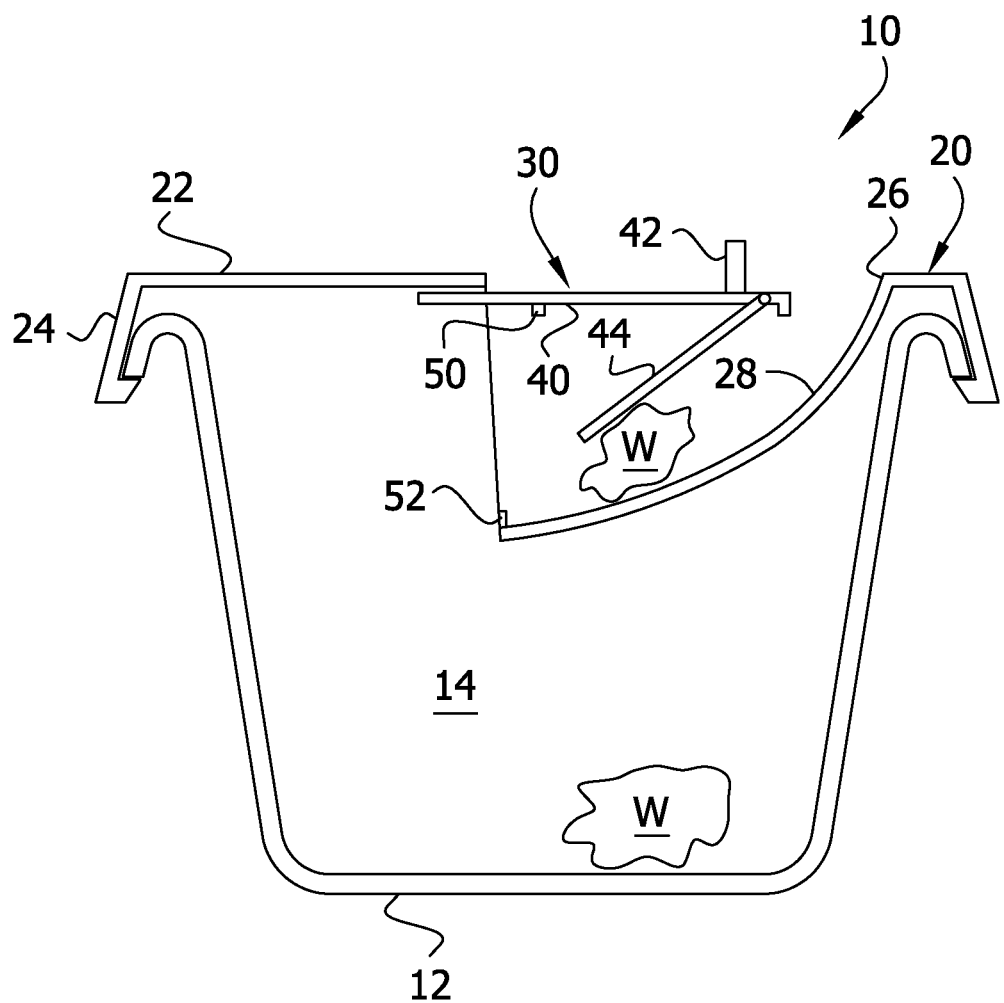
FIG. 2 is a vertical cross section of a lid of the receptacle with the cover in a partially closed position.

The closure 30 includes a door 40 having a knob 42 extending upward from it. The knob 42 permits users to move the door 40 between the open and closed positions. The door 40 may be held in the cover 22 by a track (not shown) in a conventional manner. A skirt 44 is pivotally connected to the door 40. The skirt 44 contacts the chute 28 when the closure 30 is in the open position as shown in FIG. 1. As the closure 30 is moved toward the closed position as illustrated in FIG. 2, the skirt 44 pivots upward with respect to the door 40, separates from the chute 28 and passes over any medical waste W positioned on the chute. As the closure 30 moves from the closed position (FIG. 3) to the open position (FIG. 1), the skirt 44 sweeps medical waste W on the chute 28 toward the interior 14 of the waste receptacle base 12. Those skilled in the art will appreciate that the skirt 44 is biased toward the chute 28 by gravity so that the skirt generally remains in contact with the chute unless acted upon by an upward force.

The skirt 44 includes an upper stop 50 that prevents the skirt 44 from separating from the chute 28 when the closure 30 is in the open position as shown in FIG. 1. A lower stop 52 is operatively connected to the skirt 44 for preventing the skirt from separating from the chute when the closure 30 is in the open position. As will be apparent to those skilled in the art, the upper and lower stops 50, 52 respectively, prevent users from inserting their hand into the interior of the waste receptacle 10 when the closure 30 is in the open position. The stops 50, 52 extend from one or both sides of the base 12 to limit motion of the skirt 44 without interfering with movement of waste. In one embodiment, the upper and lower stops 50, 52, respectively, are posts protruding inward from opposite sides of the base 12.

Although not described or illustrated in the embodiment discussed above, the door 40 may include a lock or latch to prevent the door from opening once the lock or latch is engaged.

Although components of the present invention may be made of other materials without departing from the scope of the present invention, in one embodiment are formed from suitable plastics, such as polypropylene, polyethylene, and combinations thereof. The components may be colored in conformance with industry standards. Because methods of making and assembling the components described above are conventional and well understood by those skilled in the art, they will not be described in this application. The base and lid may be formed from any material having suitable leak and puncture resistance and may be partially or completely transparent or translucent to monitor the level of medical waste in the base.

Having described the invention in detail, it will be apparent that modifications and variations are possible without departing from the scope of the invention defined in the appended claims.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A lid for covering an interior of a medical waste receptacle base, said lid comprising:
    a cover sized and shaped for covering the interior of the medical waste receptacle base, the cover having an opening sized for passing medical waste therethrough;
    a chute extending below the cover opening for directing medical waste into the interior of the medical waste receptacle base;
    a closure sized for blocking the opening operatively connected to the cover for movement between an open position, in which the closure is at least partially out of alignment with the opening to allow medical waste to pass through the opening toward the interior of the medical waste receptacle base, and a closed position, in which the closure is aligned with the opening to block the opening to prevent medical waste from passing through the opening; and
    a skirt operatively connected to the closure, said skirt sweeping medical waste on the chute toward the waste receptacle base interior as the closure moves from the closed position to the open position, the skirt being separable from the chute as the closure moves from the open position to the closed position to pass over medical waste positioned on the chute.

2. A lid as set forth in claim 1 wherein the closure translates with respect to the cover when moving between the open position and the closed position.

3. A lid as set forth in claim 2 wherein the skirt is pivotably connected to the closure.

4. A lid as set forth in claim 3 further comprising a stop operatively connected to the skirt for preventing the skirt from separating from the chute when the closure is in the open position.

5. A medical waste receptacle comprising:
    a base having an interior sized and shaped for receiving medical waste;
    a cover sized and shaped for covering the interior of the base, the cover having an opening sized for passing medical waste therethrough;
    a chute extending below the cover opening for directing medical waste into the interior of the base;
    a closure sized for blocking the opening operatively connected to the cover for movement between an open position, in which the closure is at least partially out of alignment with the opening to allow medical waste to pass through the opening toward the interior of the base, and a closed position, in which the closure is aligned with the opening to block the opening to prevent medical waste from passing through the opening; and
    a skirt operatively connected to the closure, said skirt sweeping medical waste on the chute toward the waste receptacle base interior as the closure moves from the closed position to the open position, the skirt being separable from the chute as the closure moves from the open position to the closed position to pass over medical waste positioned on the chute.

6. A lid for covering an interior of a medical waste receptacle base, said lid comprising:
a cover sized and shaped for covering the interior of the medical waste receptacle base, the cover having an opening sized for passing medical waste therethrough;
a chute extending below the cover opening for directing medical waste into the interior of the medical waste receptacle base;
a closure sized for blocking the opening operatively connected to the cover for movement between an open position, in which the closure is at least partially out of alignment with the opening to allow medical waste to pass through the opening toward the interior of the medical waste receptacle base, and a closed position, in which the closure is aligned with the opening to block the opening to prevent medical waste from passing through the opening; and
a skirt operatively connected to the closure, said skirt being biased toward the chute and adapted to sweep medical waste on the chute toward the interior of the medical waste receptacle base, the skirt being separable from the chute as the closure moves from the open position to the closed position to pass over medical waste positioned on the chute.

7. A lid as set forth in claim 6 wherein the skirt sweeps medical waste on the chute toward the waste receptacle base interior as the closure moves from the closed position to the open position.

8. A lid as set forth in claim 7 wherein the skirt sweeps medical waste on the chute toward the waste receptacle base interior as the closure moves from the closed position to the open position.

9. A lid as set forth in claim 6 wherein the closure translates with respect to the cover when moving between the open position and the closed position.

10. A lid as set forth in claim 9 wherein the skirt is pivotably connected to the closure.

11. A lid as set forth in claim 10 further comprising a stop operatively connected to the skirt for preventing the skirt from separating from the chute when the closure is in the open position.

12. A lid as set forth in claim 6 wherein the skirt is biased by gravity toward the chute.

13. A medical waste receptacle comprising:
a base having an interior sized and shaped for receiving medical waste;
a cover sized and shaped for covering the interior of the base, the cover having an opening sized for passing medical waste therethrough;
a chute extending below the cover opening for directing medical waste into the interior of the base;
a closure sized for blocking the opening operatively connected to the cover for movement between an open position, in which the closure is at least partially out of alignment with the opening to allow medical waste to pass through the opening toward the interior of the base, and a closed position, in which the closure is aligned with the opening to block the opening to prevent medical waste from passing through the opening; and
a skirt operatively connected to the closure, said skirt being biased toward the chute for sweeping medical waste on the chute toward the interior of the base, the skirt being separable from the chute as the closure moves from the open position to the closed position to pass over medical waste positioned on the chute.

14. A lid as set forth in claim 13 wherein the skirt sweeps medical waste on the chute toward the interior of the base as the closure moves from the closed position to the open position.

15. A lid as set forth in claim 13 wherein the skirt sweeps medical waste on the chute toward the interior of the base as the closure moves from the closed position to the open position.

* * * * *